United States Patent
Moscoso et al.

(10) Patent No.: US 8,053,618 B1
(45) Date of Patent: Nov. 8, 2011

(54) UZM-35 ZEOLITIC COMPOSITION, METHOD OF PREPARATION AND PROCESSES

(75) Inventors: Jaime G Moscoso, Mount Prospect, IL (US); Deng-Yang Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/151,482

(22) Filed: Jun. 2, 2011

Related U.S. Application Data

(63) Continuation-in-part of application No. 12/820,079, filed on Jun. 21, 2010.

(51) Int. Cl.
| | |
|---|---|
| *C07C 6/12* | (2006.01) |
| *C07C 5/22* | (2006.01) |
| *C07C 2/08* | (2006.01) |
| *C07C 25/00* | (2006.01) |

(52) U.S. Cl. ........ 585/475; 585/481; 585/533; 585/467; 585/666; 585/671; 585/739; 208/27

(58) Field of Classification Search .................. 585/475, 585/481, 533, 666, 671, 739, 467
See application file for complete search history.

(56) References Cited

U.S. PATENT DOCUMENTS

| | | | |
|---|---|---|---|
| 4,310,440 | A | 1/1982 | Wilson et al. |
| 4,440,871 | A | 4/1984 | Lok et al. |
| 5,157,196 | A | 10/1992 | Crossland et al. |
| 5,157,197 | A | 10/1992 | Cooper et al. |
| 6,049,018 | A | 4/2000 | Calabro et al. |
| 6,776,975 | B2 | 8/2004 | Wilson et al. |
| 7,578,993 | B2 | 8/2009 | Lewis et al. |

OTHER PUBLICATIONS

Lewis, Experimental Charge Density Matching Approach to Zeolite Synthesis, Studies in Surface Science and Catalysis, 2004, vol. 154A, pp. 364-372.

Rietveld, A Profile Refinement Method for Nuclear and magnetic Structures, J. Appl. Cryst., 1969, vol. 2, pp. 65-71.

*Primary Examiner* — Thuan Dinh Dang
(74) *Attorney, Agent, or Firm* — Maryann Maas

(57) ABSTRACT

A new family of crystalline aluminosilicate zeolitic compositions, UZM-35 compositions, has been synthesized. These zeolitic compositions are represented by the empirical formula.

$$M_m^{n+}R_r^{+}Al_{1-x}E_xSi_yO_z$$

where M represents a combination of potassium and sodium exchangeable cations, R is a singly charged organoammonium cation such as the dimethyldipropylammonium cation and E is a framework element such as gallium. These compositions comprise a MSE zeolite, a MFI zeolite and an ERI zeolite. The compositions are similar to MCM-68 but are characterized by unique x-ray diffraction patterns and have catalytic properties for carrying out various hydrocarbon conversion processes.

1 Claim, No Drawings

UZM-35 ZEOLITIC COMPOSITION, METHOD OF PREPARATION AND PROCESSES

CROSS-REFERENCE TO RELATED APPLICATION

This application is a Continuation-In-Part of co-pending application Ser. No. 12/820,079 filed Jun. 21, 2010, the contents of which are hereby incorporated by reference in its entirety.

FIELD OF THE INVENTION

This invention relates to a UZM-35 composition comprising a MSE zeolite, an MFI zeolite, and an ERI zeolite. The UZM-35 composition is represented by the empirical formula of:

$$M_m^{n+}R_r^+Al_{1-x}E_xSi_yO_z$$

where M represents a combination of potassium and sodium exchangeable cations, R is a singly charged organoammonium cation such as dimethyldipropylammonium and E is a framework element such as gallium.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase, which is dispersed throughout the internal voids of the crystal without significantly displacing any atoms, which make up the permanent zeolite crystal structure. Topological zeolite structure are described in *Atlas of Zeolite Framework Types*, which is maintained by the International Zeolite Association Structure Commission at http://www.iza-structure.org/databases/. Zeolites can be used as catalysts for hydrocarbon conversion reactions, which can take place on outside surfaces as well as on internal surfaces within the pore.

One particular zeolite of the MSE structure type, designated MCM-68, was disclosed by Calabro et al. in 1999 (U.S. Pat. No. 6,049,018). This patent describes the synthesis of MCM-68 from dication directing agents, N,N,N',N'-tetraalkylbicyclo[2.2.2]oct-7-ene-2R,3S:5R,6S-dipyrrolidinium dication, and N,N,N',N'-tetraalkylbicyclo[2.2.2]octane-2R,3S:5R,6S-dipyrrolidinium dication. MCM-68 was found to have at least one channel system in which each channel is defined by a 12-membered ring of tetrahedrally coordinated atoms and at least two further independent channel systems in which each channel is defined by a 10-membered ring of tetrahedrally coordinated atoms wherein the number of unique 10-membered ring channels is twice the number of 12-membered ring channels.

Applicants have successfully prepared a new family of material compositions designated UZM-35 composition. The topology of one of the zeolites in the composition is similar to that observed for MCM-68. The materials are prepared via the use of a simple commercially available structure directing agents, such as dimethyldipropylammonium hydroxide, in concert with small amounts of $K^+$ and $Na^+$ together using the Charge Density Mismatch Approach to zeolite synthesis described in U.S. Pat. No. 7,578,993. The UZM-35 zeolite having the MSE topology may be synthesized as a UZM-35 composition comprising the MSE topology zeolite as well as a MFI topology zeolite and an ERI topology zeolite. Topologies of MSE, MFI, ERI are as defined in *Atlas of Zeolite Framework Types*, which is maintained by the International Zeolite Association Structure Commission at http://www.iza-structure.org/databases/.

SUMMARY OF THE INVENTION

As stated, the present invention relates to a new aluminosilicate zeolite composition designated UZM-35 composition which comprises an MSE zeolite, a MFI zeolite and an ERI zeolite. Accordingly, one embodiment of the invention is a microporous crystalline zeolitic UZM-35 composition having a three-dimensional framework of at least $AlO_2$ and $SiO_2$ tetrahedral units and an empirical composition in the as synthesized and anhydrous basis expressed by an empirical formula of:

$$M_m^+R_r^+Al_{1-x}E_xSi_yO_z$$

where M represents a combination of potassium and sodium exchangeable cations, "m" is the mole ratio of M to (Al+E) and varies from about 0.05 to about 3, R is a singly charged organoammonium cation selected from the group consisting of dimethyldipropylammonium ($DMDPA^+$), dimethyl diisopropylammonium ($DMDIP^+$), choline, ethyltrimethylammonium ($ETMA^+$), diethyldimethylammonium ($DEDMA^+$), trimethylpropylammonium, trimethylbutylammonium, dimethyldiethanolammonium, tetraethylammonium ($TEA^+$), tetrapropylammonium ($TPA^+$), methyltripropylammonium, and mixtures thereof, "r" is the mole ratio of R to (Al+E) and has a value of about 0.25 to about 2.0, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m+r+3+4\cdot y)/2$$

and is characterized in that the composition has the x-ray diffraction pattern having at least the d-spacings and intensities set forth in Table A

TABLE A

| 2θ | d (Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |

TABLE A-continued

| 2θ | d (Å) | I/Io % |
|---|---|---|
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w |

In addition, the composition is thermally stable up to a temperature of greater than 400° C. in one embodiment and 600° C. in another embodiment. The UZM-35 composition as synthesized comprises a MSE topology zeolite, a MFI topology zeolite and an ERI topology zeolite. Typically, the amount of MSE zeolite in the composition will vary from about 55 wt % to about 75 wt. % or from about 55 wt-% to about 90 wt.-%. The amount of MFI zeolite varies from about 20 wt-% to about 35 wt-% of the composition or from about 10 wt-% to about 35 wt.-%, and the amount of ERI zeolite varies from about 3 wt-% to about 9 wt-% of the composition or from about 3 wt-% to about 10 wt.-%. Of course, the sum of the amount of the three zeolites, absent any other impurities, adds up to 100 wt % of the composition.

The crystalline microporous zeolitic UZM-35 composition described above, may be synthesized by forming a reaction mixture containing reactive sources of M, R, Al, Si and optionally E and heating the reaction mixture at a temperature of about 150° C. to about 200° C., or about 165° C. to about 185° C., for a time sufficient to form the composition, the reaction mixture having a composition expressed in terms of mole ratios of the oxides of:

$$aM_2O:bR_{2/p}O:1-cAl_2O_3:cE_2O_3:dSiO_2:eH_2O$$

where "a" has a value of about 0.05 to about 1.25, "b" has a value of about 1.5 to about 40, "p" is the weighted average valance of R and varies from 1 to about 2, "c" has a value of 0 to about 1.0, "d" has a value of about 4 to about 40, "e" has a value of about 25 to about 4000. The MSE type zeolite UZM-35 zeolite is synthesized along with additional zeolites MFI and ERI to form the UZM-35 composition.

Yet another embodiment of the invention is a hydrocarbon conversion process using the UZM-35 composition. The process comprises contacting the hydrocarbon with the UZM-35 composition at conversion conditions to give a converted hydrocarbon.

DETAILED DESCRIPTION OF THE INVENTION

Applicants have prepared an aluminosilicate zeolitic composition which comprises a MSE zeolite, a MFI zeolite, and an ERI zeolite. The MSE zeolite has a topological structure that is related to MSE as described in *Atlas of Zeolite Framework Types* and thus will be called an MSE zeolite herein. As will be shown in detail, the UZM-35 composition is different from MCM-68 in a number of its characteristics. The microporous crystalline zeolitic UZM-35 composition has an empirical composition in the as-synthesized form and on an anhydrous basis expressed by the empirical formula:

where M represents a combination of potassium and sodium exchangeable cations. R is a singly charged organoammonium cation, examples of which include but are not limited to the dimethyldipropylammonium cation (DMDPA$^+$), dimethyldiisopropylammonium (DMDIP$^+$), choline [(CH$_3$)$_3$N(CH$_2$)$_2$OH]$^+$, ETMA$^+$, DEDMA$^+$, trimethylpropylammonium, trimethylbutylammonium, dimethyldiethanolammonium, methyltripropylammonium, TEA$^+$, TPA$^+$ and mixtures thereof and "r" is the mole ratio of R to (Al+E) and varies from about 0.25 to about 2.0 while "m" is the mole ratio of M to (Al+E) and varies from about 0.05 to about 3. The mole ratio of silicon to (Al+E) is represented by "y" which varies from about 2 to about 30. E is an element which is tetrahedrally coordinated, is present in the framework and is selected from the group consisting of gallium, iron and boron. The mole fraction of E is represented by "x" and has a value from 0 to about 1.0, while "z" is the mole ratio of O to (Al+E) and is given by the equation:

$$z=(m\cdot n+r+3+4\cdot y)/2.$$

Where M is only one metal, then the weighted average valence is the valence of that one metal, i.e. +1 or +2. However, when more than one M metal is present, the total amount of:

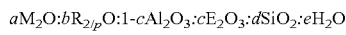

and the weighted average valence "n" is given by the equation:

$$n = \frac{m_1 \cdot n_1 + m_2 \cdot n_2 + m_3 \cdot n_3 + \ldots}{m_1 + m_2 + m_3 + \ldots}$$

The microporous crystalline zeolitic UZM-35 composition is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals, potassium and sodium, include the halide salts, nitrate salts, acetate salts, and hydroxides of the respective alkali metals. R is an organoammonium cation selected from the group consisting of dimethyldipropylammonium, choline, ETMA, DEDMA, TEA, TPA, trimethylpropylammonium, trimethylbutylammonium, dimethyldiethanolammonium and mixtures thereof, and the sources include the hydroxide, chloride, bromide, iodide and fluoride compounds. Specific examples include without limitation dimethyldipropylammonium hydroxide, dimethyldipropylammonium chloride, dimethyldipropylammonium bromide, dimethyldiisopropylammonium hydroxide, dimethyldiisopropylammonium chloride, dimethyldiisopropylammonium bromide ethyltrimethylammonium hydroxide, diethyldimethylammonium hydroxide, tetraethylammonium hydroxide, tetrapropylammonium hydroxide, and tetrapropylammonium chloride.

Note that during synthesis, the metal M is +1 valance, specifically potassium and sodium. However, in an alternative embodiment, the composition may undergo additional ion exchange steps post synthesis to provide a material with one or more metals, M, having a +2 valance.

The reaction mixture containing reactive sources of the desired components can be described in terms of molar ratios of the oxides by the formula:

$$aM_2O:bR_{2/p}O:1-cAl_2O_3:cE_2O_3:dSiO_2:eH_2O$$

where "a" varies from about 0.05 to about 1.25, "b" varies from about 1.5 to about 40, "c" varies from 0 to 1.0, "d" varies from about 4 to about 40, and "e" varies from about 25 to about 4000. If alkoxides are used, it is preferred to include a distillation or evaporative step to remove the alcohol hydrolysis products. The reaction mixture is now reacted at a temperature of about 150° C. to about 200° C., about 165° C. to about 185° C., or about 170° C. to about 180° C., for a period of about 1 day to about 3 weeks and preferably for a time of about 5 days to about 12 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. It should be pointed out that UZM-35 zeolite seeds can optionally be added to the reaction mixture in order to accelerate the formation of the composition.

A preferred synthetic approach to make UZM-35 composition utilizes the charge density mismatch concept, which is disclosed in U.S. Pat. No. 7,578,993 and *Studies in Surface Science and Catalysis*, (2004), Vol. 154A, 364-372. The method disclosed in U.S. Pat. No. 7,578,993 employs quaternary ammonium hydroxides to solubilize aluminosilicate species, while crystallization inducing agents such as alkali and alkaline earth metals and more highly charged organoammonium cations are often introduced in a separate step. Once some UZM-35 seeds have been generated using this approach, the seeds can be used in a single step synthesis of the UZM-35 composition, using, for example, a combination of dimethyldipropylammonium hydroxide and the alkali cations. The use of commercially available dimethyldipropylammonium hydroxide to prepare the UZM-35 composition offers a great economic advantage over the structure directing agents previously employed (N,N,N',N'-tetraalkylbicyclo[2.2.2]oct-7-ene-2R,3S:5R,6S-dipyrrolidinium dication, and N,N,N',N'-tetraalkylbicyclo[2.2.2]octane-2R,3S:5Rs,6-dipyrrolidinium dication) to prepare aluminosilicates with the MSE topology. Additionally, dimethyldipropyl ammonium hydroxide can be employed as the hydroxide or the chloride in concert with other inexpensive organoammonium hydroxides using the charge density mismatch concept to reduce costs even further.

The UZM-35 composition, which is obtained from the above-described process, is characterized by the x-ray diffraction pattern using the Rietveld refinement method described in J. Appl. Cryst. (1969) 2, 65-71, and having at least the d-spacings and relative intensities set forth in Table A below.

TABLE A

| 2θ | d (Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w |

As will be shown in detail in the examples, the UZM-35 composition is thermally stable up to a temperature of at least 400° C. and in another embodiment, up to about 600° C.

As synthesized, the UZM-35 composition will contain some of the exchangeable or charge balancing cations in its pores. These exchangeable cations can be exchanged for other cations, or in the case of organic cations, they can be removed by heating under controlled conditions. Because UZM-35 composition comprises large pore zeolite(s), it is also possible to remove some organic cations directly by ion exchange. The UZM-35 composition may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Properties that are modified include porosity, adsorption, Si/Al mole ratio, acidity, thermal stability, etc.

The UZM-35 compositions which are modified by one or more techniques described in the '975 patent (herein UZM-35HS) are described by the empirical formula on an anhydrous basis of:

$$M1_a^{n+}Al_{(1-x)}E_xSi_{y'}O_{z'}$$

where M1 is at least one exchangeable cation selected from the group consisting of alkali, alkaline earth metals, rare earth metals, ammonium ion, hydrogen ion and mixtures thereof, "a" is the mole ratio of M1 to (Al+E) and varies from about 0.05 to about 50, "n" is the weighted average valence of M1 and has a value of about +1 to about +3, E is an element selected from the group consisting of gallium, iron, boron, and mixtures thereof, "x" is the mole fraction of E and varies from 0 to 1.0, y' is the mole ratio of Si to (Al+E) and varies from greater than about 4 to virtually pure silica and z' is the mole ratio of O to (Al+E) and has a value determined by the equation:

$$z'=(a \cdot n+3+4 \cdot y')/2$$

By virtually pure silica is meant that virtually all the aluminum and/or the E metals have been removed from the framework. It is well know that it is virtually impossible to remove all the aluminum and/or E metal. Numerically, a zeolite is virtually pure silica when y' has a value of at least 3,000, preferably 10,000 and most preferably 20,000. Thus, ranges for y' are from 4 to 3,000 preferably greater than 10 to about 3,000; 4 to 10,000 preferably greater than 10 to about 10,000 and 4 to 20,000 preferably greater than 10 to about 20,000.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The crystalline zeolitic UZM-35 composition of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The UZM-35 composition of this invention can also be used as a catalyst or catalyst support in various hydrocarbon conversion processes. Hydrocarbon conversion processes are well known in the art and include cracking, hydrocracking, alkylation of both aromatics and isoparaffin, isomerization of paraffin and poly-alkylbenzenes such as xylene, trans-alkylation of poly-alkybenzene with benzene or mono-alkybenzenes, disproportionation of mono-alkybenzenes, polymerization, reforming, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. No. 4,310,440 and U.S. Pat. No. 4,440,871 which are hereby incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of about 204° C. to about 649° C. (400° to 1200° F.) or about 316° C. to about 510° C. (600° F. and 950° F.). Reaction pressures are in the range of atmospheric to about 24,132 kPa g (3,500 psig), or between about 1379 to about 20,685 kPa g (200 to 3000 psig). Contact times usually correspond to liquid hourly space velocities (LHSV) in the range of about 0.1 hr$^{-1}$ to 15 hr$^{-1}$, preferably between about 0.2 and 3 hr$^{-1}$. Hydrogen circulation rates are in the range of 178 to about 8,888 std. m$^3$/m$^3$ (1,000 to 50,000 standard cubic feet (scf) per barrel of charge), or about 355 to about 5,333 std. m$^3$/m$^3$ (about 2,000 to about 30,000 scf per barrel of charge). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the UZM-35 composition using feedstocks such as gas oils, heavy naphthas, deasphalted crude oil residua, etc. with gasoline being the principal desired product. Temperature conditions of about 454° C. to about 593° C. (about 850° F. to about 1100° F.), LHSV values of 0.5 to 10 and pressure conditions of from about 0 to about 344 kPa g (about 0 to 50 psig) are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 1:1 and 30:1, a olefin LHSV of about 0.3 to about 10 hr$^{-1}$, a temperature of about 100° to about 250° C. and pressures of about 1379 kPa g to about 6895 kPa g (about 200 to about 1000 psig). Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,895 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The following examples are presented in illustration of this invention and are not intended as undue limitations on the generally broad scope of the invention as set out in the appended claims.

The structure of the UZM-35 composition of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of $100 \times I/I_o$, the above designations are defined as:

w=0-15; m=15-60: s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only illustration and are not intended as an undue limitation on the broad scope of the invention as set forth in the appended claims.

EXAMPLE 1

An aluminosilicate reaction solution was prepared by first mixing 16.64 aluminum hydroxide (27.78 mass-% Al) and 526.79 g dimethyldipropylammonium hydroxide, 18.8 mass-% solution, while stirring vigorously. After thorough mixing, 252.98 g of Ludox™ AS-40 (40% SiO$_2$) was added. The reaction mixture was homogenized for an additional hour with a high speed mechanical stirrer and placed in an oven at 100° C. overnight. Analysis showed the resulting aluminosilicate solution contained 6.52 wt. % Si and 0.64 wt. % Al yielding a Si/Al ratio of 9.78.

To a 150 g portion of the aluminosilicate solution prepared in Example 1, a composite aqueous NaOH/KOH solution containing 1.44 g of NaOH (98%) and 2.02 g of KOH dissolved in 20.0 g distilled water was added with vigorous stirring and the reaction mixture was homogenized for an additional 30 minutes. A 24 g portion of the reaction mixture was transferred to a 45 ml Parr stainless steel autoclave which was heated to 175° C. and maintained at that temperature for 120 hrs. The solid product was recovered by centrifugation, washed with de-ionized water, and dried at 100° C.

The solid products were recovered by centrifugation, washed with de-ionized water and dried at 95° C. The product was identified as UZM-35 zeolite by xrd. Representative diffraction lines observed for the product are shown in Table 1. The product composition was determined by elemental analysis to consist of the following mole ratios: Si/Al=7.92, Na/Al=0.1, K/Al=0.48.

TABLE 1

| 2θ | d(Å) | I/I$_o$ % |
|---|---|---|
| 6.65 | 13.26 | m |
| 6.95 | 12.69 | m |
| 8.10 | 10.90 | m |
| 8.87 | 9.95 | m |
| 9.76 | 9.05 | m |
| 10.83 | 8.13 | w |
| 13.76 | 6.43 | w |
| 15.22 | 5.81 | w |

TABLE 1-continued

| 2θ | d(Å) | I/I$_o$ % |
|---|---|---|
| 18.00 | 4.92 | w |
| 19.46 | 4.55 | m |
| 19.62 | 4.52 | m |
| 20.06 | 4.42 | m |
| 20.63 | 4.3 | m |
| 21.1 | 4.20 | m |
| 21.76 | 4.08 | vs |
| 21.92 | 4.05 | m |
| 22.07 | 4.03 | m |
| 22.55 | 3.93 | m |
| 22.73 | 3.90 | m |
| 23.08 | 3.85 | s |
| 23.42 | 3.79 | m |
| 23.51 | 3.77 | m |
| 24.04 | 3.69 | m |
| 24.53 | 3.62 | w |
| 25.9 | 3.43 | m |
| 25.99 | 3.42 | w |
| 26.27 | 3.38 | m |
| 26.92 | 3.3 | m |
| 27.57 | 3.23 | m |
| 27.76 | 3.21 | m |
| 28.17 | 3.16 | m |
| 28.86 | 3.09 | w |
| 29.27 | 3.04 | m |
| 29.72 | 3.00 | w |
| 30.26 | 2.95 | w |
| 30.91 | 2.88 | m |
| 31.38 | 2.84 | w |
| 33.61 | 2.68 | w |
| 34.65 | 2.58 | w |
| 35.43 | 2.53 | w |
| 36.18 | 2.48 | w |
| 41.77 | 2.16 | w |
| 44.7 | 2.02 | w |
| 45.32 | 1.99 | w |
| 45.63 | 1.98 | w |
| 46.55 | 1.94 | w |
| 47.62 | 1.90 | w |
| 47.94 | 1.89 | w |
| 49.70 | 1.83 | w |
| 51.06 | 1.78 | w |

Scanning Electron Microscopy (SEM) revealed crystals of square shaped morphology, approximately 100 by 350 nm in size. This sample was calcined at 540° C. for 10 hrs under nitrogen and then air. Representative diffraction lines observed for the calcined product are shown in Table 2.

TABLE 2

| 2θ | d(Å) | I/I$_o$ % |
|---|---|---|
| 6.72 | 13.13 | m |
| 7.02 | 12.57 | vs |
| 8.0 | 11.04 | m |
| 8.2 | 10.77 | m |
| 8.3 | 10.64 | m |
| 8.98 | 9.83 | m |
| 9.87 | 8.94 | vs |
| 11.00 | 8.03 | m |
| 11.29 | 7.82 | w |
| 13.85 | 6.38 | m |
| 14.17 | 6.24 | w |
| 14.95 | 5.91 | w |
| 15.04 | 5.88 | w |
| 17.72 | 4.99 | w |
| 17.90 | 4.95 | w |
| 19.56 | 4.53 | m |
| 19.64 | 4.51 | m |
| 19.70 | 4.50 | m |
| 20.16 | 4.40 | m |
| 20.64 | 4.29 | w |
| 21.15 | 4.19 | w |
| 21.86 | 4.06 | vs |

TABLE 2-continued

| 2θ | d(Å) | I/I₀% |
|---|---|---|
| 21.98 | 4.04 | s |
| 22.07 | 4.02 | m |
| 22.62 | 3.92 | m |
| 22.72 | 3.91 | s |
| 23.27 | 3.91 | vs |
| 24.08 | 3.69 | m |
| 24.69 | 3.60 | w |
| 25.29 | 3.51 | w |
| 26.28 | 3.38 | m |
| 27.12 | 3.28 | m |
| 27.66 | 3.22 | m |
| 28.28 | 3.15 | m |
| 28.98 | 3.07 | w |
| 29.36 | 3.03 | m |
| 29.99 | 2.97 | w |
| 30.38 | 2.93 | m |
| 31.02 | 2.88 | m |
| 31.54 | 2.83 | w |
| 33.46 | 2.67 | w |
| 34.68 | 2.58 | w |
| 35.07 | 2.55 | w |
| 35.84 | 2.50 | w |
| 36.29 | 2.47 | w |
| 39.37 | 2.28 | w |
| 41.92 | 2.15 | w |
| 44.96 | 2.01 | w |
| 45.72 | 1.98 | w |
| 46.74 | 1.94 | w |
| 47.82 | 1.9 | w |
| 48.13 | 1.88 | w |
| 49.75 | 1.83 | w |

EXAMPLE 2

An aluminosilicate reaction solution was prepared by first mixing 37.17 g of aluminum hydroxide (27.78 mass-% Al) and 1053.58 g of dimethyldipropylammonium hydroxide (18.8 mass-% solution), while stirring vigorously. After thorough mixing, 505.96 g Ludox™ AS-40 (SiO₂, 40%) was added. The reaction mixture was homogenized for 1 hour with a high speed mechanical stirrer, sealed in a Teflon bottle and placed in an oven overnight at 100° C. Analysis showed the aluminosilicate solution contained 6.16 wt. % Si and 0.67 wt. % Al (Si/Al=8.83).

A 100.0 g portion of the above aluminosilicate solution was continuously stirred. A composite aqueous solution containing 2.38 g of KOH and 0.3 g of NaOH dissolve in 15 g $H_2O$ was added, dropwise, to the aluminosilicate solution. After the addition was completed, the resulting reaction mixture was homogenized for 1 hour, transferred to (4) 45 ml Parr stainless steel autoclave which was heated to 175° C. and maintained at that temperature for 216 hrs. The solid product was recovered by centrifugation, washed with de-ionized water, and dried at 100° C.

The solid product from each of these samples was recovered by centrifugation, washed with de-ionized water and dried at 95° C. The products resulting from all four reactions were identified by xrd to be UZM-35 zeolite. Table 3 shows representative diffraction lines observed for the sample that was reacted for 9 days. Elemental analysis gave a product composition in mole ratios of: Si/Al=7.58, Na/Al=0.033, K/Al=0.63, C/N=6, N/Al=0.43.

TABLE 3

| 2θ | d(Å) | I/I₀% |
|---|---|---|
| 6.56 | 13.46 | m |
| 6.84 | 12.91 | s |
| 8.10 | 10.90 | m |
| 8.80 | 10.03 | m |
| 9.69 | 9.11 | m |
| 10.80 | 8.18 | w |
| 13.69 | 6.45 | w |
| 14.17 | 6.01 | w |
| 15.10 | 5.86 | w |
| 15.88 | 5.57 | w |
| 18.01 | 4.91 | w |
| 19.48 | 4.55 | w |
| 19.98 | 4.44 | m |
| 20.52 | 4.32 | w |
| 21.00 | 4.22 | m |
| 21.68 | 4.09 | vs |
| 22.49 | 3.94 | m |
| 23.04 | 3.85 | s |
| 24.31 | 3.65 | m |
| 24.61 | 3.61 | w |
| 25.85 | 3.44 | m |
| 26.14 | 3.40 | m |
| 26.85 | 3.31 | m |
| 27.68 | 3.22 | m |
| 28.15 | 3.16 | m |
| 29.20 | 3.05 | m |
| 29.90 | 2.98 | m |
| 30.82 | 2.89 | m |
| 31.33 | 2.85 | w |
| 32.49 | 2.75 | w |
| 33.28 | 2.68 | w |
| 34.42 | 2.60 | w |
| 34.84 | 2.57 | w |
| 35.32 | 2.53 | w |
| 35.69 | 2.51 | w |
| 36.10 | 2.48 | w |
| 37.59 | 2.39 | w |
| 41.75 | 2.16 | w |
| 44.67 | 2.02 | w |
| 45.11 | 2.00 | w |
| 45.45 | 1.99 | w |
| 46.10 | 1.96 | w |
| 46.50 | 1.95 | w |
| 47.01 | 1.93 | w |
| 47.62 | 1.90 | w |
| 49.7 | 1.83 | w |

EXAMPLE 3

An aluminosilicate reaction solution was prepared by first mixing 37.17 g of aluminum hydroxide (27.78% Al) and 1053.58 g of dimethyldipropylammonium hydroxide (18.8 mass-% solution), while stirring vigorously. After thorough mixing, 505.96 g Ludox™ AS-40 (SiO₂, 40 mass-%) was added. The reaction mixture was homogenized for 1 hour with a high speed mechanical stirrer, sealed in a Teflon bottle and placed in an oven overnight at 100° C. Analysis showed the aluminosilicate solution contained 6.16 wt. % Si and 0.67 wt. % Al (Si/Al mole ratio=8.83).

A 1200 g portion of the above aluminosilicate solution was continuously stirred. A composite aqueous solution containing 28.56 g of KOH and 3.6 g of NaOH dissolve in 150 g $H_2O$, was added, dropwise, to the aluminosilicate solution. After the addition was completed, the resulting reaction mixture was homogenized for 1 hour, transferred to a 2000 ml Parr stainless steel autoclave which was heated to 175° C. and maintained at that temperature for 216 hrs. The solid product was recovered by centrifugation, washed with de-ionized water, and dried at 100° C.

The solid product from each of these samples was recovered by centrifugation, washed with de-ionized water and dried at 95° C. The products resulting from this reaction were identified by xrd to be UZM-35 zeolite. Elemental analysis gave a product composition in mole ratios of: Si/Al=7.57, Na/Al=0.028, K/Al=0.73, N/Al=0.37. This sample was calcined at 540° C. for 10 hrs under nitrogen and then air. Representative diffraction lines observed for the product are shown in Table 4.

TABLE 4

| 2θ | d(Å) | I/I₀ % |
|---|---|---|
| 6.54 | 13.5 | m |
| 6.85 | 12.88 | m |
| 8.10 | 10.90 | m |
| 8.82 | 10.01 | m |
| 9.67 | 9.13 | m |
| 10.80 | 8.18 | m |
| 11.08 | 7.97 | w |
| 13.67 | 6.46 | m |
| 14.84 | 5.96 | w |
| 15.21 | 5.81 | w |
| 15.61 | 5.67 | w |
| 15.91 | 5.56 | w |
| 17.47 | 5.07 | w |
| 17.87 | 4.95 | w |
| 19.52 | 4.54 | m |
| 19.96 | 4.44 | m |
| 20.54 | 4.32 | m |
| 21.16 | 4.19 | m |
| 21.67 | 4.09 | vs |
| 21.89 | 4.05 | s |
| 22.54 | 3.94 | s |
| 23.08 | 3.85 | vs |
| 24.45 | 3.63 | m |
| 24.65 | 3.60 | w |
| 25.06 | 3.55 | m |
| 25.84 | 3.44 | m |
| 26.14 | 3.40 | m |
| 26.46 | 3.36 | m |
| 26.90 | 3.31 | m |
| 27.48 | 3.21 | m |
| 27.73 | 3.21 | m |
| 28.19 | 3.16 | m |
| 28.66 | 3.11 | w |
| 29.18 | 3.05 | m |
| 29.58 | 3.01 | w |
| 29.88 | 2.98 | m |
| 30.21 | 2.95 | m |
| 30.80 | 2.90 | m |
| 31.38 | 2.84 | w |
| 33.32 | 2.68 | w |
| 34.52 | 2.59 | w |
| 34.79 | 2.57 | w |
| 35.69 | 2.51 | w |
| 36.15 | 2.48 | w |
| 41.70 | 2.16 | w |
| 44.83 | 2.01 | w |
| 45.46 | 1.99 | w |
| 46.52 | 1.95 | w |
| 47.54 | 1.91 | w |
| 47.88 | 1.89 | w |
| 49.56 | 1.83 | w |

EXAMPLE 4

This example describes the modification of a UZM-35 material. A 10 g portion of a UZM-35 sample (Si/Al mole ratio 7.57) was calcined in a nitrogen atmosphere, ramping at 3° C./min to 540° C. and holding there for an additional hour before changing the atmosphere to air and continuing the calcination for another 9 hr. A solution was prepared by first diluting 2 g of HNO₃ (69 mass-%) followed by dissolving 10 g of NH₄NO₃ in 120 g de-ionized water. This solution was heated to 75° C. before adding the calcined UZM-35. The slurry was stirred for 1 hr at 75° C. The product was isolated by filtration, washed with de-ionized water and dried at 100° C. for 12 hrs.

The product was identified as UZM-35HS via x-ray powder diffraction. Elemental analyses confirmed an increase in Si/Al mole ratio to Si/Al=8.3, Na/Al=0.01, K/Al=0.44.

EXAMPLE 5

This example demonstrates the modification of a UZM-35 material. A 20 g portion of a UZM-35 sample (Si/Al mole ratio 7.57) was calcined under a nitrogen atmosphere by ramping at 3° C./min to 560° C. and holding there for 1 hr before changing the atmosphere to air and continuing the calcination for another 9 hr. Separately, a solution was prepared by dissolving 20 g of NH₄NO₃ in 490 g de-ionized water. The solution was heated to 75° C. before adding the calcined UZM-35. The slurry was stirred for 1 hr at 75° C. The product was isolated by filtration, washed with de-ionized water and dried at 100° C. for 12 hrs.

The product was identified as UZM-35HS via x-ray powder diffraction. Elemental analyses of this sample shows a Si/Al mole ratio to Si/Al=8.0, Na/Al=0.01, K/Al=0.47.

EXAMPLE 6

An aluminosilicate solution was prepared by first mixing 37.17 g aluminum hydroxide (27.78 mass-% Al) and 1053.58 g dimethyldipropylammonium hydroxide, 18.8 mass-% solution, with vigorous stirring. After thorough mixing, 505.96 g of Ludox™ AS-40 (40 mass-% SiO₂) was added. The reaction mixture was homogenized for an additional hour with a high speed mechanical stirrer and placed in an oven at 100° C. overnight. Analysis showed the resulting aluminosilicate solution contained 6.16 wt. % Si and 0.67 wt. % Al yielding a Si/Al mole ratio of 8.83.

To a 100 g portion of the aluminosilicate solution prepared in Example 6 above, an aqueous NaOH solution containing 1.98 g of NaOH (98%) in 10.0 g distilled water was added with vigorous stirring and the reaction mixture was homogenized for an additional 30 minutes. A 24 g portion of the reaction mixture was transferred to a 45 ml Parr stainless steel autoclave which was heated to 175° C. and maintained at that temperature for 144 hrs. The solid product was recovered by centrifugation, washed with de-ionized water, and dried at 100° C.

The solid products were recovered by centrifugation, washed with de-ionized water and dried at 95° C. The product was identified as MOR zeolite by xrd.

EXAMPLE 7

An aluminosilicate solution was prepared by first mixing 37.17 aluminum hydroxide (27.78 mass % Al) and 1053.58 g dimethyldipropylammonium hydroxide, 18.8 mass-% solution, with vigorous stirring. After thorough mixing, 505.96 g of Ludox™ AS-40 (40 mass-% SiO₂) was added. The reaction mixture was homogenized for an additional hour with a high speed mechanical stirrer and placed in an oven at 100° C. overnight. Analysis showed the resulting aluminosilicate solution contained 6.16 wt.-%-Si and 0.67 wt.-% Al yielding a Si/Al mole ratio of 8.83.

To a 150 g portion of the aluminosilicate solution prepared in Example 6, an aqueous KOH solution containing 3.84 g of KOH dissolved in 20.0 g distilled water was added with vigorous stirring and the reaction mixture was homogenized for an additional 30 minutes. A 24 g portion of the reaction mixture was transferred to a 45 ml Parr stainless steel autoclave which was heated to 175° C. and maintained at that temperature for 264 hrs. The solid product was recovered by centrifugation, washed with de-ionized water, and dried at 100° C.

The solid products were recovered by centrifugation, washed with de-ionized water and dried at 95° C. The product was identified as ZSM-5 zeolite by xrd.

EXAMPLE 8

An aluminosilicate reaction solution was prepared by first mixing 86.33 g of aluminum hydroxide (26.97 mass-% Al) and 1437.67 g of dimethyldipropylammonium hydroxide (40.66 mass-% solution), while stirring vigorously. After thorough mixing, 1366.88 g Ludox™ AS-40 ($SiO_2$, mass-40%) was added. The reaction mixture was homogenized for 20 minutes with a high-speed mechanical stirrer, the aluminosilicate colloidal solution was continuously stirred and an aqueous solution containing 83.04 g of KOH and 17.38 g of NaOH dissolved in 808.7 g $H_2O$, was added, drop wise, to the aluminosilicate solution. After the addition was completed, the resulting reaction mixture was homogenized for ½ hour, transferred to (3) 2000 ml Parr stainless steel autoclave which were heated to 175° C. and maintained at that temperature for 9 days. The solid products were recovered by filtration, washed with de-ionized water, and dried at 100° C.

The product resulting from this reaction was identified by x-ray diffraction (Rietveld refinement method described in J. Appl. Cryst. (1969) 2, 65-71) to be a UZM-35 composition of 72.1 wt-% MSE type zeolite with a lattice parameter of 18.372 angstroms for a and 20.285 angstroms for c; 24.1 wt-% MFI zeolite with a lattice parameter of 20.101 angstroms for a, 19.862 angstroms for b and 13.402 for c, and 3.7 wt-% ERI zeolite with a lattice parameter of 13.222 angstroms for a and 14.900 angstroms for c. Chemical analysis gave a product composition of mole ratio Si/Al=8.9. BET Surface area was determined to be 408 m2/g and micropore volume was 0.197 cc/g. Representative diffraction lines observed for the product are shown in Table 5.

TABLE 5

| 2θ | d (Å) | I/Io % |
|---|---|---|
| 6.5 | 13.58 | m |
| 6.8 | 12.99 | s |
| 7.79 | 11.32 | m |
| 8.07 | 10.93 | m |
| 8.719 | 10.13 | m |
| 9.63 | 9.17 | s |
| 10.75 | 8.21 | w |
| 13.63 | 6.49 | w |
| 14.74 | 6.00 | w |
| 15.56 | 5.69 | w |
| 15.86 | 5.58 | w |
| 19.46 | 4.55 | m |
| 19.899 | 4.45 | m |
| 20.518 | 4.32 | m |
| 20.94 | 4.23 | w |
| 21.618 | 4.1 | vs |
| 21.799 | 4.07 | s |
| 22.399 | 3.96 | m |
| 22.93 | 3.87 | s |
| 23.299 | 3.81 | m |
| 23.78 | 3.73 | m |
| 24.82 | 3.58 | w |
| 25.76 | 3.45 | w |
| 26.09 | 3.41 | m |
| 26.74 | 3.33 | m |
| 27.42 | 3.24 | m |
| 28.04 | 3.17 | w |
| 29.10 | 3.06 | w |
| 29.54 | 3.02 | w |

TABLE 5-continued

| 2θ | d (Å) | I/Io % |
|---|---|---|
| 29.75 | 2.99 | w |
| 30.13 | 2.96 | m |
| 30.73 | 2.9 | m |
| 31.47 | 2.83 | w |
| 33.19 | 2.69 | w |
| 34.46 | 2.6 | w |
| 35.18 | 2.54 | w |
| 35.59 | 2.51 | w |
| 36.04 | 2.49 | w |
| 41.65 | 2.16 | w |
| 44.57 | 2.03 | w |
| 47.48 | 1.91 | w |
| 49.53 | 1.83 | w |

This sample was calcined at 600° C. for 5 hrs under nitrogen and then air. The product resulting from the calcination was identified by x-ray diffraction (Rietveld refinement method described in J. Appl. Cryst. (1969) 2, 65-71) to be a mixture of 64.4 wt % UZM-35 with a lattice parameter of 18.371 angstroms for a and 20.235 angstroms for c; 30.7 wt % MFI with a lattice parameter of 20.048 angstroms for a, 19.880 angstroms for b and 13.403 angstroms for c, and 4.8 wt % ERI with a lattice parameter of 13.071 angstroms for a and 15.238 angstroms for c. A 160 g portion of the calcined UZM-35 sample (Si/Al mole ratio of 8.9) was NH4 exchanged. A solution was prepared by dissolving 160 g of $NH_4NO_3$ in 1800 g de-ionized water. The solution was heated to 75° C. before adding the calcined UZM-35. The slurry was stirred for 1 hr at 75° C. The product was isolated by filtration, washed with de-ionized water. This NH4 exchange procedure was repeated 3 times then it was dried at 100° C. for 12 hrs.

Elemental analyses of this sample shows a Si/Al mole ratio to Si/Al=9.07, Na/Al=0.01, K/Al=0.11.

Representative diffraction lines observed for the product are shown in Table 6.

TABLE 6

| 2θ | d (Å) | I/Io % |
|---|---|---|
| 6.67 | 13.22 | m |
| 6.97 | 12.65 | m-s |
| 7.94 | 11.12 | m |
| 8.14 | 10.85 | m |
| 8.93 | 9.88 | m |
| 9.79 | 9.01 | m-s |
| 10.92 | 8.09 | m |
| 13.78 | 6.42 | w |
| 14.1 | 6.27 | w |
| 14.97 | 5.91 | w |
| 15.7 | 5.63 | w |
| 16.05 | 5.51 | w |
| 17.57 | 5.04 | w |
| 19.64 | 4.51 | m |
| 20.05 | 4.42 | m |
| 20.65 | 4.29 | m |
| 21.13 | 4.19 | w |
| 21.77 | 4.07 | vs |
| 21.98 | 4.04 | s-vs |
| 22.62 | 3.92 | s |
| 23.14 | 3.84 | vs |
| 23.46 | 3.78 | m |
| 23.94 | 3.71 | m |
| 24.58 | 3.61 | w |
| 24.83 | 3.58 | w |
| 25.2 | 3.53 | m |
| 25.92 | 3.43 | w |
| 26.24 | 3.39 | m |
| 26.52 | 3.35 | m |
| 26.96 | 3.3 | m |
| 27.6 | 3.22 | m-s |

TABLE 6-continued

| 2θ | d (Å) | I/Io % |
|---|---|---|
| 28.25 | 3.15 | m |
| 28.79 | 3.09 | m |
| 29.3 | 3.04 | m |
| 29.68 | 3 | w |
| 29.96 | 2.98 | m |
| 30.35 | 2.94 | m |
| 30.89 | 2.89 | m |
| 31.46 | 2.84 | m |
| 31.81 | 2.81 | m |
| 33.4 | 2.68 | m |
| 36.22 | 2.47 | w |
| 41.83 | 2.15 | w |
| 44.86 | 2.01 | w |
| 47.64 | 1.9 | w |
| 49.69 | 1.83 | w |

EXAMPLE 9

An aluminosilicate reaction solution was prepared by first mixing 29.01 g of aluminum hydroxide (26.97 wt. % Al) and 483.08 g of dimethyldipropylammonium hydroxide (40.66% solution), while stirring vigorously. After thorough mixing, 461.58 g Ludox™ AS-40 ($SiO_2$, 40 wt. %) was added. The reaction mixture was homogenized for 20 minutes with a high-speed mechanical stirrer, the aluminosilicate colloidal solution was continuously stirred and an aqueous solution containing 27.90 g of KOH and 3.46 g of NaOH dissolved in 269.98 g $H_2O$, was added, drop wise, to the aluminosilicate solution. After the addition was completed, the resulting reaction mixture was homogenized for ½ hour, transferred to a 2000 ml Parr stainless steel autoclave, which was heated to 175° C. and maintained at that temperature for 10 days. The solid products were recovered by filtration, washed with de-ionized water, and dried at 100° C.

The product resulting from this reaction was identified by x-ray diffraction (Rietveld refinement method described in J. Appl. Cryst. (1969) 2, 65-71) to be a UZM-35 composition of 66.3 wt % MSE type zeolite with a lattice parameter of 18.369 angstroms for a and 20.284 angstroms for c; 25.5 wt % MFI with a lattice parameter of 20.136 angstroms for a, 19.976 angstroms for b and 13.443 angstroms for c, and 8.2 wt % ERI with a lattice parameter of 13.152 angstroms for a and 15.107 angstroms for c. Chemical analysis gave a product composition (mole ratio) of Si/Al=7.65, N/Al=0.38, K/Al=0.68, Na/Al=0.03. BET surface area was determined to be 404 m2/g and a micropore volume was 0.188 cc/g. Representative diffraction lines observed for the product are shown in Table 7.

TABLE 7

| 2θ | d (Å) | I/Io % |
|---|---|---|
| 6.48 | 13.32 | 31.9 |
| 6.78 | 13.02 | 58.5 |
| 8.05 | 10.96 | 25.7 |
| 8.71 | 10.13 | 33.6 |
| 9.61 | 9.18 | 53.6 |
| 10.75 | 8.21 | 11.2 |
| 13.61 | 6.49 | 12.9 |
| 14.74 | 6 | 7.3 |
| 15.86 | 5.58 | 7.2 |
| 19.48 | 4.55 | 41.5 |
| 19.9 | 4.45 | 21.1 |
| 20.5 | 4.32 | 13.4 |
| 20.96 | 4.23 | 25.6 |
| 21.61 | 4.1 | 100 |
| 21.81 | 4.07 | 63.8 |
| 22.42 | 3.96 | 45.7 |
| 22.94 | 3.87 | 85.5 |
| 23.3 | 3.81 | 38.5 |
| 23.5 | 3.78 | 31.3 |
| 23.86 | 3.72 | 17.8 |
| 24.41 | 3.64 | 6.8 |
| 25.78 | 3.45 | 20.2 |
| 26.09 | 3.41 | 19.8 |
| 26.81 | 3.32 | 39.8 |
| 27.14 | 3.28 | 20.9 |
| 27.44 | 3.24 | 42.9 |
| 27.69 | 3.21 | 33 |
| 28.06 | 3.17 | 14.7 |
| 29.15 | 3.06 | 16.2 |
| 29.55 | 3.01 | 13.5 |
| 29.86 | 2.98 | 20.8 |
| 30.14 | 2.96 | 18.7 |
| 30.75 | 2.9 | 24.1 |
| 31.26 | 2.85 | 8.9 |
| 33.21 | 2.69 | 11.1 |
| 34.34 | 2.6 | 8.8 |
| 34.76 | 2.57 | 10.5 |
| 35.2 | 2.54 | 6.8 |
| 35.57 | 2.52 | 8.6 |
| 36.02 | 2.49 | 8 |
| 41.71 | 2.16 | 9.8 |
| 44.61 | 2.02 | 8.2 |
| 47.48 | 1.91 | 8 |
| 49.56 | 1.83 | 10.1 |

This sample was calcined at 600° C. for 5 hrs under nitrogen and then air. The product resulting from the calcination was identified by x-ray diffraction (Rietveld refinement method described in J. Appl. Cryst. (1969) 2, 65-71) to be a UZM-35 composition of 61.9 wt-% MSE zeolite with a lattice parameter of 18.401 angstroms for a and 20.280 angstroms for c; 30.8 wt-% MFI zeolite with a lattice parameter of 20.114 angstroms for a, 19.919 angstroms for b and 13.432 angstroms for c, and 7.3-wt % ERI zeolite with a lattice parameter of 13.189 angstroms for a and 15.174 angstroms for c. This sample was calcined at 600° C. for 5 hrs under nitrogen and then air. The product resulting from the calcination was identified by x-ray diffraction (Rietveld refinement method described in J. Appl. Cryst. (1969) 2, 65-71) to be a UZM-35 composition of 61.9 wt-% MSE zeolite with a lattice parameter of 18.401 angstroms for a and 20.280 angstroms for c; 30.8 wt-% MFI zeolite with a lattice parameter of 20.114 angstroms for a, 19.919 angstroms for b and 13.432 angstroms for c, and 7.3-wt % ERI zeolite with a lattice parameter of 13.189 angstroms for a and 15.174 angstroms for c. A 100 g portion of the calcined UZM-35 sample (Si/Al mole ratio=7.65) was NH4 exchanged. A solution was prepared by dissolving 160 g of $NH_4NO_3$ in 1800 g de-ionized water. The solution was heated to 75° C. before adding the calcined UZM-35. The slurry was stirred for 1 hr at 75° C. The product was isolated by filtration, washed with de-ionized water. This NH4 exchange procedure was repeated 3 times then it was dried at 100° C. for 12 hrs.

Elemental analyses of this sample shows a Si/Al mole ratio to Si/Al=9.20, Na/Al=0.01, K/Al=0.10.

Representative diffraction lines observed for the product are shown in Table 8.

TABLE 8

| 2θ | d (Å) | I/Io % |
|---|---|---|
| 6.5 | 13.58 | m |
| 6.81 | 12.95 | m |
| 7.98 | 11.07 | m |
| 8.76 | 10.08 | m |
| 9.63 | 9.16 | m |
| 10.77 | 8.2 | m |
| 13.63 | 6.48 | m |
| 14.8 | 5.98 | w |
| 15.84 | 5.58 | w |
| 19.51 | 4.54 | m |
| 19.91 | 4.45 | m |
| 20.49 | 4.32 | m |
| 21.01 | 4.22 | m |
| 21.62 | 4.1 | vs |
| 22.49 | 3.94 | s |
| 23.02 | 3.86 | vs |
| 23.3 | 3.81 | m-s |
| 23.64 | 3.76 | m |
| 23.91 | 3.71 | m |
| 24.41 | 3.64 | m |
| 24.62 | 3.61 | w |
| 25.11 | 3.54 | w |
| 25.81 | 3.44 | m |
| 26.09 | 3.41 | m |
| 26.41 | 3.37 | m |
| 26.86 | 3.31 | m-s |
| 27.45 | 3.24 | m-s |
| 27.65 | 3.22 | m |
| 28.13 | 3.16 | m |
| 28.82 | 3.09 | w |
| 29.14 | 3.06 | m |
| 29.57 | 3.01 | w |
| 29.84 | 2.99 | m |
| 30.21 | 2.95 | m |
| 30.76 | 2.9 | m |
| 31.31 | 2.85 | w |
| 33.27 | 2.69 | w |
| 36.12 | 2.48 | w |
| 41.68 | 2.16 | w |
| 44.74 | 2.02 | w |
| 47.56 | 1.91 | w |
| 49.57 | 1.83 | w |

The invention claimed is:

1. A hydrocarbon conversion process is selected from the group consisting of alkylation, trans-alkylation, isomerization, olefin dimerization, olefin oligomerization, and dewaxing comprising contacting a hydrocarbon stream with a UZM-35HS composition catalyst at hydrocarbon conversion conditions to give a converted product, the UZM-35HS composition catalyst comprising a MFI zeolite, an ERI zeolite, and a MSE zeolite, wherein the UZM-35HS zeolite has a three-dimensional framework of at least $AlO_2$ and $SiO_2$ tetrahedral units and an empirical composition on an anhydrous basis expressed by an empirical formula of:

$$M1_a^{n+}Al_{(1-x)}E_xSi_{y'}O_{z'}$$

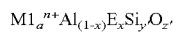

where M1 is at least one exchangeable cation selected from the group consisting of alkali, alkaline earth metals, rare earth metals, ammonium ion, hydrogen ion and mixtures thereof, "a" is the mole ratio of M1 to (Al+E) and varies from about 0.05 to about 50, "n" is the weighted average valence of M1 and has a value of about +1 to about +3, E is an element selected from the group consisting of gallium, iron, boron, and mixtures thereof, "x" is the mole fraction of E and varies from 0 to 1.0, y' is the mole ratio of Si to (Al+E) and varies from greater than about 4 to virtually pure silica and z' is the mole ratio of O to (Al+E) and has a value determined by the equation:

$$z'=(a \cdot n+3+4 \cdot y')/2$$

and is characterized in that it has the x-ray diffraction pattern having at least the d-spacings and intensities set forth in Table A:

TABLE A

| 2θ | d (Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w | and is thermally stable up to a temperature of at least 400° C.

* * * * *